(12) United States Patent
Lin et al.

(10) Patent No.: US 8,802,834 B2
(45) Date of Patent: *Aug. 12, 2014

(54) SUCROSE POLYESTERS

(75) Inventors: Peter Yau-Tak Lin, Liberty Township, OH (US); Deborah Jean Back, Cleves, OH (US); Donald Benjamin Appleby, Cincinnati, OH (US); James M. Robertson, Kansas City, MO (US); Steven Robert Baker, Kansas City, MO (US)

(73) Assignee: The Procter & Gamble Compnay, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/479,327

(22) Filed: May 24, 2012

(65) Prior Publication Data

US 2012/0330000 A1 Dec. 27, 2012

Related U.S. Application Data

(60) Provisional application No. 61/500,472, filed on Jun. 23, 2011.

(51) Int. Cl.
| | | |
|---|---|---|
| C11C 3/04 | (2006.01) | |
| C11C 3/00 | (2006.01) | |
| A23D 9/013 | (2006.01) | |
| A23L 1/308 | (2006.01) | |
| A23L 1/307 | (2006.01) | |

(52) U.S. Cl.
CPC ............... *A23L 1/3088* (2013.01); *C11C 3/00* (2013.01); *A23D 9/013* (2013.01); *C11C 3/04* (2013.01); *A23L 1/307* (2013.01)
USPC .......................................... 536/18.2

(58) Field of Classification Search
CPC ......... A23L 1/3088; C11C 3/04; A23D 9/013
USPC .......................................... 536/18.2
See application file for complete search history.

(56) References Cited

U.S. PATENT DOCUMENTS

| 4,822,875 A | 4/1989 | McCoy |
| 4,835,001 A | 5/1989 | Mijac |
| 4,952,687 A | 8/1990 | Bodor |
| 5,085,884 A | 2/1992 | Young |
| 5,532,019 A | 7/1996 | Miller |
| 2011/0129592 A1 | 6/2011 | Appleby |

FOREIGN PATENT DOCUMENTS

EP 0384508 A2 8/1990

*Primary Examiner* — Brandon Fetterolf
*Assistant Examiner* — Yih-Horng Shiao
(74) *Attorney, Agent, or Firm* — Melissa G Krasovec; Melody A Jones

(57) ABSTRACT

Disclosed herein are compositions that include a blend of sucrose polyesters, wherein each sucrose polyester includes a sucrose moiety and a plurality of fatty acid ester moieties, wherein from about 50% to about 90%, by weight, of the combined fatty acid ester moieties of the sucrose polyesters in the blend are palmitic fatty acid ester moieties.

18 Claims, No Drawings

SUCROSE POLYESTERS

CROSS-REFERENCE TO RELATED APPLICATIONS

This application claims priority under 35 U.S.C. §119(e) to U.S. Provisional Application Ser. No. 61/500,472, filed Jun. 23, 2011.

FIELD OF THE INVENTION

This disclosure relates to high-palmitic sucrose polyester compositions, as well as methods of making and using such compositions.

BACKGROUND OF THE INVENTION

One of the most common health problems among people today is obesity. The condition is linked to ingestion of a greater number of calories than are expended. Fat comprises a concentrated source of calories in a person's diet, and thus, there remains a continuing need to reduce and/or replace fat in food products. One way of reducing and/or replacing fat content in food products is through the employment of non-digestible fats (e.g., sucrose polyesters). Because replacing higher percentages of fat with sucrose polyester ("SPE") will correspondingly lower the number of calories in a food product, there is a continuing need for sucrose polyester containing compositions.

Sucrose polyesters, because of their bulk and shape, form different crystalline structures having melting profiles that are quite dissimilar to certain natural fats and oils. Typically, sucrose polyesters meeting the compositional restrictions of Olestra®, as approved by the United States Food and Drug Administration, have a very flat melting profile across a broad temperature range. By fully hydrogenating sucrose polyesters, it is possible to increase the melting point by converting sucrose polyesters containing unsaturated carbon chains into sucrose polyesters containing saturated carbon chains; however, the melting profile of such sucrose polyesters remains flat, resulting in a high solids content at body temperatures (approximately 37° C.). When these fully hydrogenated sucrose polyesters are incorporated into food products, such a high solids content causes an undesirable, waxy mouth feel for the consumer eating the food product. This is particularly disadvantageous when the sucrose polyesters are incorporated into cheese, chocolate or other confections because such products are favored by the consumer, in part, due to a particular mouth feel associated with these types of products. In other words, certain food products (e.g., cheese, chocolates, frostings, icings, ice creams, etc.) may be particularly preferred because of the products' ability to melt in a consumer's mouth.

An alternate way to combat the flat melting profile of sucrose polyesters is though a hydrogenation process that coverts only a portion of the double bonds to saturated fatty acids, coverts another portion of the double bonds to trans fatty acids and leaves the remaining double bonds unchanged (remaining in the cis configuration). The resulting sucrose polyester composition has a broad melting point range and this material is a type of what is typically referred to as an intermediate melting fraction ("IMF") Like the fully hydrogenated sucrose polyesters, the IMF sucrose polyester composition also has a significant amount of solids at body temperature (i.e., greater than 10%). When used at 100% to produce food products, the finish products have waxy mouth feel and are found to be poorly accepted.

Thus, there remains a continuing need for a fat substitute that can be incorporated into food products, wherein the fat substitute provides a consumer with a desired mouth-feel when eating the food products.

SUMMARY OF THE INVENTION

High-palmitic sucrose polyester compositions, and methods of making and using such compositions, are disclosed herein.

In one embodiment, the present disclosure provides for a composition comprising a blend of sucrose polyesters, wherein each sucrose polyester comprises a sucrose moiety and a plurality of fatty acid ester moieties, wherein from about 90% to about 100% of the sucrose polyesters in the blend are selected from a group consisting of octa-, hepta-, and hexa-sucrose polyesters, from about 50% to about 75% of the combined fatty acid ester moieties of the sucrose polyesters in the blend are palmitic fatty acid ester moieties, and from about 50% to about 90% of the combined fatty acid ester moieties of the sucrose polyesters in the blend comprise a $C_{16}$ carbon chain, with the balance of the fatty acid ester moieties of the sucrose polyesters in the blend comprising a carbon chain independently selected from $C_{12}$-$C_{14}$ or $C_{18}$-$C_{22}$ carbon chains.

In another embodiment, the present disclosure provides for processes of making the above detailed sucrose polyesters that include the step of transesterifying a sucrose molecule with an ester, the ester being produced via esterifying a fractionated oil that comprises a palmitic fatty acid content of from about 50% to about 90% with a lower alcohol.

DETAILED DESCRIPTION OF THE INVENTION

As used herein, the articles "a" and "an" when used in a claim, are understood to mean one or more of what is claimed or described.

As used herein, the terms "include", "includes" and "including" are meant to be non-limiting.

As used herein, the term "comprising" means various components conjointly employed in the preparation of the compositions of the present disclosure. Accordingly, the terms "consisting essentially of" and "consisting of" are embodied in the term "comprising".

As used herein, the "complete melting point" means the temperature at which the last visible traces of solids disappear. The complete melting point of a given composition or component is measured in accordance with AOCS Method Cc 1-25 (American Oil Chemists' Society).

As used herein, the term "lower alcohol" means a $C_1$, $C_2$, $C_3$, or $C_4$ alcohol, and combinations thereof.

As used herein, the term "melting point" means the temperature at which a component starts to change from the solid to the liquid phase.

As used herein, the term "octa-sucrose polyester," means that eight of the available hydroxyl moieties on a sucrose molecule are esterified with a fatty acid; the term "hepta-sucrose polyester" means that seven of the available hydroxyl moieties on a sucrose molecule are esterified with a fatty acid; the term "hexa-sucrose polyester" means that six of the available hydroxyl moieties on a sucrose molecule are esterified with a fatty acid; the term "penta-sucrose polyester" means that five of the available hydroxyl moieties on a sucrose molecule are esterified with a fatty acid.

As used herein, "Solid Fat Content" or "SFC" means the percentage of a fat or oil that exists in crystalline form at a given temperature.

As used herein, the Solid Fat Index, or "SFI" is an empirical measure of solid fat content (SFC) at standardized temperature check points.

As used herein, the term "sucrose polyester" means a molecule comprising a sucrose moiety and a plurality of fatty acid moieties, wherein at least five of the available hydroxyl groups on the sucrose molecule are esterified with a fatty acid.

As used herein, "palmitic fatty acid ester" means a completely saturated fatty acid ester that is 16 carbons long (i.e., palmitic fatty acid methyl ester is $CH_3(CH_2)_{14}COOCH_3$).

As used herein, "palmitic fatty acid content" means the percentage of palmitic fatty acid esters, when compared with the total number of fatty acid esters, in a given composition.

As used herein, "high-palmitic sucrose polyesters" means sucrose polyesters with at least 50% palmitic fatty acid content.

As used herein, all tests and measurements, unless otherwise specified, are made at 25° C.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

To be useful in cheese, chocolates and other confections (e.g., coatings, frosting, fillings, icings, baked goods, candy, ice cream and other food products), non-caloric fat substitutes are ideally solid at room temperature but have a melting point near or at body temperature. The melting point and melting profile of the non-caloric fat substitutes utilized in cheese, chocolates and other confections contribute to the desired mouth-feel associated with these types of food products. Ideally, the non-caloric fat substitutes will contain little to no solids at body temperature (about 37° C.). As stated above, a problem in the art as it relates to employing sucrose polyesters in these types of food products is the ability to provide a food product that delivers a desired mouth feel to the consumer.

Creating a desired mouth feel in sucrose polyester containing products may be achieved by increasing the slope of the SFC curve (curve created by charting solid percentage versus temperature) of the sucrose polyester composition. One method of increasing the slope of the SFC curve of the sucrose polyester composition is through incorporation of a certain amount of trans content into the composition. For example, U.S. patent application Ser. No. 12/957,759 discloses high-trans sucrose polyester compositions that have high level of solids at room temperature while having relatively low level of solids at body temperature when compared to prior sucrose polyester compositions. It has now surprisingly been discovered that sucrose polyester compositions comprising high palmitic acid content (as further detailed herein) also have high level of solids at room temperature while having relatively low level of solids at mouth temperature when compared to previous sucrose polyester compositions. Accordingly, when such high-palmitic sucrose polyesters are incorporated into food products, the resulting food products impart consumers with less waxy mouth feel.

In another aspect, when compared to the high-trans sucrose polyester compositions of U.S. patent application Ser. No. 12/957,759, the high-palmitic sucrose polyester compositions disclosed herein possess faster rates of crystallization. Speed in the crystallization of a composition is very important for the ability to commercialize a given composition. Before a sucrose polyester composition can be packaged and transported, the composition must be sufficiently crystallized. Accordingly, two similar sucrose polyester compositions with different crystallization rates will have significantly different production costs. The composition with the faster crystallization rate will have a lower production cost than the composition with the slower crystallization rate. This is because the composition with the slower crystallization rate will need extra conveyer time, cooling tunnel time and/or production space to accommodate the longer production time. Further, a shortening composition that incorporates a sucrose polyester composition with slower crystallization rate is less desirable because the texture of the shortening will continue to become more firm over time. The firmness of the shortening might be at a desired level when the shortening is first shipped to a customer, but becomes too stiff over an extended storage time. Alternatively, if the shortening is shipped to a customer before the firmness has increased to a desired level, the customer might have to wait for weeks or months before such firmness level is obtained. Accordingly, the high-palmitic sucrose polyester compositions detailed herein possess the added surprising advantage of a faster rate of crystallization when compared to high-trans sucrose polyester compositions.

One way of estimating the rate of crystallization is by determining the amount of solids formed (degree of crystallization) at different temperatures using a differential scanning calorimeter (at a set of predetermined parameters—see method below). When observing and comparing the amount of solids formed for sucrose polyester compositions, compositions with higher amounts of solids at a given temperature have greater crystallization rates. The chosen temperatures of this method were relevant to critical temperatures of shortening and chocolate production processes. 25° C. is close to the temperature of a shortening as it exits a votator and is also near the chocolate tempering temperature. 5° C. is approximately the temperature of the scrape wall heat exchanger for shortening processing. The degree of crystallization for the high-palmitic sucrose polyester composition further detailed below in Example 3 is 26.7% @ 25° C. and 87.6% @ 5° C. The degree of crystallization for the high-trans sucrose polyester composition as detailed in Example 3 of U.S. patent application Ser. No. 12/957,759 is 13.6% @ 25° C. and 63.9% @ 5° C. This indicates that the high-palmitic sucrose polyester crystallization rate is greater than the high-trans sucrose polyester crystallization rate.

Further, the degree of crystallization for a typical sucrose polyester composition (as detailed below in Example 4—Olestra® w/Post Hydrogenation) is 39.4% @ 25° C. and 83.8% @ 5° C. Although the degrees of crystallization of this material are higher at 25° C. and lower at 5° C. than the degrees of crystallization of the high-palmitic sucrose polyester composition detailed in Example 3, this typical sucrose polyester composition also possesses a much higher level of solids at 40° C. (also reported below in Example 4). This high level of solids at 40° C. produces a significant amount of waxiness in finished products made with this typical sucrose polyester composition when such composition is used at a high level.

Accordingly, disclosed herein are high-palmitic sucrose polyesters having a melting profile such that compositions containing such sucrose polyesters provide consumers a desired mouth feel suited for cheese, chocolate, confections, or other like food products. Such high-palmitic sucrose polyesters also have increased rates of crystallization when compared to high-trans sucrose polyester compositions. Processes of making such sucrose polyesters, and shortening compositions that comprise such sucrose polyesters, are also disclosed herein.

Sucrose Polyester:

Disclosed herein are compositions comprising a blend of sucrose polyesters, wherein each sucrose polyester comprises a sucrose moiety and a plurality of fatty acid ester moieties, wherein:

a. from about 90% to about 100%, or from about 95% to about 100%, by weight, of the sucrose polyesters in the blend are selected from a group consisting of octa-, hepta-, and hexa-sucrose polyesters;

b. from about 50% to about 75%, or from about 55% to about 70%, or from about 60% to about 65%, by weight, of the combined fatty acid ester moieties of the sucrose polyesters in the blend are palmitic fatty acid ester moieties; and c. from about 50% to about 90%, or from about 55% to about 75%, or from about 55% to about 65%, by weight, of the combined fatty acid ester moieties of the sucrose polyesters in the blend comprise a $C_{1-6}$ carbon chain, with the balance of the fatty acid ester moieties of the sucrose polyesters in the blend comprising a carbon chain independently selected from $C_{12}$-$C_{14}$ or $C_{18}$-$C_{22}$ carbon chains.

In one aspect, about 10% to about 50%, or about 25% to about 50%, of the combined fatty acid ester moieties of the sucrose polyesters in the blend may comprise an unsaturated carbon chain.

In one aspect, the compositions may comprise a degree of crystallization at 25° C. of about 15% to about 40%, or from about 20% to about 35%, or from about 22% to about 30%, or from about 24% to about 28%. Further, the compositions may comprise a degree of crystallization at 5° C. of about 70% to about 95%, or from about 75% to about 92%, or from about 80% to about 90%, or from about 84% to about 89%.

In one aspect, the compositions may comprise a fatty acid ester derived from an edible oil comprising at least one palmitic fatty acid. In one aspect, the edible oil comprising a palmitic fatty acid may be selected from rapeseed oil, tallow oil, coconut oil, babassu oil, corn oil, lard, olive oil, peanut oil, sesame oil, soybean oil, canola oil, palm oil, palm stearin, palm kernel, sunflower oil, safflower oil, cottonseed oil, cottonseed stearin and combinations thereof, and in certain cases the oil or oil combinations may be fractionated to increase the palmitic acid content.

In one aspect, the compositions may exhibit a thixotropic area of from about 50,000 to about 300,000, or from about 100,000 to about 200,000 pascals/second at 33.3° C., as measured using the Test Methods described herein. In one aspect, the composition may exhibit a thixotropic area of from about 50,000 to about 100,000 pascals/second at 33.3° C., as measured using the Test Methods described herein.

In one aspect, the compositions may comprise:

a) from about 60% to about 99%, based on the total weight of the sucrose polyester blend, of sucrose polyesters having a solid content of about 1% to about 10% at about 40° C.; and b) from about 1% to about 40%, or from about 2% to about 20%, or from about 5% to about 8%, based on the total weight of the sucrose polyester blend, of sucrose polyesters having a complete melting point of from about 40° C. to about 100° C., or from about 60° C. to about 75° C.;

wherein the composition exhibits a thixotropic area of from about 50,000 to about 300,000 pascals/second at 33.3° C.

In one aspect, the compositions may comprise, based on total weight of the sucrose polyester blend, from about 0% to about 0.5% penta-sucrose polyesters.

In one aspect, the compositions may have a Solid Fat Index such that the composition comprises, based on total weight of the sucrose polyester blend:

a) from about 45% to about 85%, or from about 65% to about 75%, solids at 10° C.;

b) from about 10% to about 50%, or from about 30% to about 40%, solids at 30° C.; and c) from about 1% to about 10%, or from about 7% to about 10%, solids at 40° C.

In one aspect, processes of making compositions as described herein are disclosed. In one aspect, the processes may comprise a step of transesterifying a sucrose molecule with an ester, the ester being produced via esterification of a fractionated oil comprising a palmitic fatty acid content of from about 50% to about 90%, with a lower alcohol.

In one aspect, the processes may comprise the steps of:

a.) fractionating an oil or methyl ester derived from an oil to produce an oil or methyl ester that comprises a palmitic fatty acid content of from about 50% to about 90%, or from about 55% to about 75%, or from about 55% to about 65%, using an oil source with palmitic content of about 20% to about 50%; and b.) transesterifying a sucrose molecule with said oil or methyl ester that comprises a palmitic fatty acid content of from about 50% to about 90%, or from about 55% to about 75%, or from about 55% to about 65%, to produce an esterified sucrose molecule that comprises a palmitic fatty acid content of from about 50% to about 90%, or from about 55% to about 75%, or from about 55% to about 65%.

In one aspect of the processes detailed above, the oil may comprise an edible oil. In one aspect, the oil may comprise an oil selected from coconut oil, babassu oil, cottonseed oil, cottonseed stearin, palm oil, palm olein, palm stearin, palm kernel, and combinations thereof.

Sucrose polyester blends that include sucrose polyesters that are produced by the processes detailed above may have a preferred mouth feel when eaten by consumers when compared to post hydrogenated sucrose polyesters.

In one aspect, shortening compositions comprising the sucrose polyester compositions as described herein are disclosed.

Test Methods

For purposes of the present application, Solid Fat Content; Palmitic Content; Thixotropic Area and Fatty Acid Composition are determined as follows:

Solid Fat Content ("SFC")—A sample of the test composition is heated to a temperature of 140° F. (60° C.) for at least 30 minutes or until the sample is completely melted. The melted sample is then tempered as follows: at 80° F. (26.7° C.) for 15 minutes; at 32° F. (0° C.) for 15 minutes; at 80° F. (26.7° C.) for 30 minutes; and at 32° F. (0° C.) for 15 minutes. After tempering, the SFC values of the sample at temperatures of 50° F. (10° C.), 70° F. (21.1° C.), 80° F. (26.7° C.), 92° F. (33.3° C.) and 98.6° F. (37° C.), is determined by pulsed nuclear magnetic resonance (PNMR) after equilibration for 30 minutes at each temperature. The method for determining SFC values by PNMR is described in Madison and Hill, J. Amer. Oil Chem. Soc., Vol. 55 (1978), pp. 328-31. Measurement of SFC by PNMR is also described in A.O.C.S. Official Method Cd. 16-81, Official Methods and Recommended Practices of The American Oil Chemists Society. 3rd. Ed., 1987.

Determination of Thixotropic Area—Samples are prepared by transferring about 8.0 grams of sample into a 57 mm aluminum pan. The sample is heated to above 113° C. until completely liquid, then tempered by cooling to 29° C. with agitation. The sample is then held at 21° C. for 7 days. Using a suitable cone and plate rheometer (such as Contraves Rheomat 115A, cone CP-6) maintained at 37.8° C. and capable of measuring the non-Newtonian flow curve hysteresis for ascending and descending shear rates programmed from 0 to 800 s-1, the rheometer is held at 0 s-1 for 120 seconds, then raised to 800 sec-1 in 7.5 minutes, held for 1 s, then decreased to 0 s-1 in 7.5 min to measure the thixotropic area. The rheometer accuracy is checked with viscosity standards such as Cannon ASTM Certified Viscosity Standards, S-2000 and N-350 or equivalent. A sufficient amount of the test sample is placed on the rheometer plate to fill the gap between the plate and cone. The thixotropic area is then measured.

Determination of the Fatty Acid Composition and Palmitic Content—The fatty acid composition of the sucrose polyesters disclosed may be measured by gas chromatography. First, fatty acid methyl esters of the sucrose polyesters are prepared via any standard method known in the art (for example, via transesterification using sodium methoxide), and then separated on a capillary column (Supelco SP2340, 60×0.32 mm×0.2 micron), utilizing a Hewlett-Packard Model 6890 gas chromatograph equipped with a Flame Ionization Detector and a Hewlett-Packard automatic sampler, Model 7683. The fatty acid methyl esters are separated by chain length, degree of unsaturation and isomeric variations including cis, palmitic and conjugation. The method is programmed to run for 50 minutes ramping the temperature from 140-195° C. with and injection temperature of 250° C. and a detection temperature of 325° C. For calibration, the fatty acid methyl ester reference standard Nuchek Prep (#446) is used.

Determination of the Degree of Crystallization—The degree of crystallization is determined using a differential scanning calorimeter (DSC). Using a TA Instrument DSCQ1000, the sample (~5 mg) is placed in a hermetically sealed pan. The DSC is programmed to heat from room temperature to 80° C. at a rate of 10° C./minute, hold at 80° C. for 1 minute to completely melt the sample, and then cool to −40° C. at a rate of 10° C./minute to crystallize the sample. The data analysis integrated the area under the curve from −20° C. to 50° C. and then reported the percent crystallized as area percent at 25° C. and 5° C.

EXAMPLES

Example 1

20 kilograms of palm stearin (available from Felda IFFCO, Cincinnati, Ohio) are placed in a 30 liter reaction vessel equipped with a stirrer and reflux condenser and reacted with 5375 grams of methanol using 226.6 grams of sodium methoxide as catalyst. The mixture is stirred at 65° C. for 6 hours; methanol is allowed to reflux. The reaction mixture is then allowed to rest without stirring until the glycerin byproduct settles to the bottom of the vessel. The glycerin layer is then removed and the methyl ester layer is washed with 10% water by weight of the methyl ester at 30° C. to remove residual methanol, catalyst, soap and any remaining glycerin. The wash process is repeated two additional times. The methyl esters are then dried under vacuum (25 mm Hg) at 95° C. The methyl esters are then distilled in a wiped film evaporator at 195° C. and ~1 mm Hg absolute pressure to separate the methyl esters from any un-reacted glycerides. The methyl esters have the following fatty acid composition:

| | |
|---|---|
| $C_{16}$ | 57.8% |
| $C_{18}$ | 6.9% |
| $C_{18:1}$ cis | 27.5% |
| $C_{18:2}$ cis | 5.9% |

Example 2

A sucrose polyester sample is prepared using the methyl ester prepared in Example 1. 1073 grams of the methyl ester of Example 1, 212 grams of a milled mixture of sucrose and potassium palmitate and 4.5 grams of potassium carbonate are added to a 5 liter reaction vessel equipped with overhead mechanical stirrer, heating mantel and nitrogen sparge tube. The contents of the reaction flask are heated to 135° C. with vigorous stirring and nitrogen sparge for ~3 hours. Another 1073 grams of the methyl ester of Example 1 is then added along with 4.5 grams of $K_2CO_3$. The reaction is continued at 135° C. until the total conversion of sucrose polyester measures >75% octa-ester.

The crude reaction mix from above is then hydrated with ~230 mL water and the contents of the flask are allowed to sit without stirring. The top layer (oil layer) is decanted away from the hydrated soap layer. The oil layer is then dried at 95° C. (25 mm Hg) until free of residual water. The oil layer is then bleached with 1% Trisyl (available from W.R. Grace) and pressure filtered to remove the bleaching earth. The treated oil layer is then passed through a wiped film evaporator to remove residual methyl esters. The resulting sucrose polyester has the following properties:

| Sucrose ester distribution | |
|---|---|
| Sucrose octa-ester | 77.1% |
| Sucrose hepta-ester | 22.9% |
| Sucrose hexa-ester | 0% |
| Sucrose penta-ester | 0% |
| Fatty Acid Composition | |
| $C_{16}$ | 59.5% |
| $C_{18}$ | 6.0% |
| $C_{18:1}$ cis | 28.1% |
| $C_{18:2}$ cis | 6.1% |

Example 3

93 grams of the sucrose polyester from Example 2 are combined with 7 grams of a solid sucrose polyester component having a melting point of 65° C. to give a sucrose polyester blend. The solid sucrose polyester component has the following properties:

| Sucrose ester distribution of the Solid Component | |
|---|---|
| Sucrose octa-ester | 77.8% |
| Sucrose hepta-ester | 22.0% |
| Sucrose hexa-ester | 0% |
| Sucrose penta-ester | 0.2% |
| Fatty Acid Composition of the Solid Component | |
| $C_{16}$ | 2.7% |
| $C_{18}$ | 3.6% |
| $C_{18:1}$ cis | 4.8% |
| $C_{18:2}$ cis | 6.2% |
| $C_{20:0}$ | 9.7% |
| $C_{22:0}$ | 71.9% |

The resulting sucrose polyester blend (comprising the sucrose polyester from Example 2 and the above detailed solid sucrose polyester component) has the following properties:

| Sucrose ester distribution | |
|---|---|
| Sucrose octa-ester | 77.2% |
| Sucrose hepta-ester | 22.8% |
| Sucrose hexa-ester | 0% |
| Fatty Acid Composition | |
| $C_{16}$ | 56.0% |
| $C_{18}$ | 5.3% |
| $C_{18:1}$ trans | 0% |
| $C_{18:1}$ cis | 26.8% |
| $C_{18:2}$ trans | 0% |
| $C_{18:2}$ trans | 5.2% |
| $C_{20:0}$ | 1.0% |
| $C_{22:2}$ | 4.8% |

Thixotropic area: 55,000 Pa/sec @ 33.3° C.

| SFC | |
|---|---|
| 10° C. | 64.4% |
| 20° C. | 45.9% |
| 30° C. | 17.6% |
| 40° C. | 5.5% |

Example 4

The properties of the sucrose polyester blend of Example 3 were compared to those of a commercially available sucrose polyester blend marketed by The Procter & Gamble Company under the Olean® brand name (referred to below as Olestra® w/Post Hydrogenation). The particular Olean® product utilized in this example is produced from partially hydrogenated soybean oil, in which the hydrogenation conditions are chosen to minimize the formation of trans fatty acid isomers. The fatty acid composition and Solid Fat Contents of both samples are compared below:

| | Sample Blend from Example 3 | Olestra ® w/Post Hydrogenation |
|---|---|---|
| Fatty Acid Composition | | |
| $C_{16}$ | 56.0% | 11.7% |
| $C_{18}$ | 5.3% | 42.0% |
| $C_{18:1}$ trans | 0% | 20.4% |
| $C_{18:1}$ cis | 26.8% | 21.8% |
| $C_{18:2}$ trans | 0% | 0.7% |
| $C_{18:2}$ trans | 5.2% | 0.7% |
| $C_{20:0}$ | 1.0% | 0% |
| $C_{22:2}$ | 4.8% | 0% |
| SFC | | |
| 10° C. | 64.4% | 52.1% |
| 20° C. | 45.9% | 29.0% |
| 30° C. | 17.6% | 21.8% |
| 40° C. | 5.5% | 13.3% |
| Sucrose ester distribution | | |
| Sucrose octa-ester | 77.2% | 78.5% |
| Sucrose hepta-ester | 22.8% | 21.2% |
| Sucrose hexa-ester | 0% | 0.3% |
| Sucrose penta-ester | 0% | 0% |

Example 5

All Purpose Shortening Composition 2.0 Kg of the sucrose polyester blend detailed in Example 3, 5.5 Kg of commercially available liquid fraction Soybean Olean®, 0.8 Kg of Trancendim® 130 (available from Caravan Ingredients, Lenexa, Kans.), and 1.7 Kg of soybean oil are fully melted and mixed in a Votator SM3\41A to form a shortening composition.

The Soybean Olean® employed in this shortening composition has the following properties:

| | Olean ® brand olestra |
|---|---|
| Fatty Acid Composition | |
| $C_{16}$ | 12.7% |
| $C_{18}$ | 6.7% |
| $C_{18:1}$ trans | 13.5% |
| $C_{18:1}$ cis | 40.3% |
| $C_{18:2}$ trans | 3.0% |
| $C_{18:2}$ cis | 17.4% |
| $C_{18:3}$ cis | 0.5% |
| $C_{20}$ | 0.7% |
| $C_{22}$ | 3.5% |
| SFC | |
| 10° C. | 10.8% |
| 20° C. | 7.6% |
| 30° C. | 6.1% |
| 40° C. | 5.6% |
| Sucrose ester distribution | |
| Sucrose octa-ester | 80.5% |
| Sucrose hepta-ester | 19.2% |
| Sucrose hexa-ester | 0.3% |
| Sucrose penta-ester | 0% |

Thixotropic area 52,000 Pa/sec @ 33.3° C.

Votator Settings:

| Feed Tank Temp. | 68° C. |
|---|---|
| Nitrogen | 90 psi |
| Post A unit | 9.8° C. |
| Exit Temp. | 15.3° C. |
| Rate | 184-186 lb/hr |
| Back Pressure | 1.78 bars |
| Tempering | 70° F. |

The resulting shortening composition has the following properties:
SFC Values

| | |
|---|---|
| SFC @ 10° C. | 29.0 |
| SFC @ 20° C. | 22.8 |
| SFC @ 30° C. | 15.3 |
| SFC @ 40.0° C. | 5.7 |

Calorie per 100 g: 225 cal
Firmness: 119,000 Pa
Yield Value: 2750 Pa
Fat Crystal Particle Size: 1-3 um
Weight Percentage of Shortening that is Sucrose Polyester: 75%

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising a blend of sucrose polyesters, wherein each sucrose polyester comprises a sucrose moiety and a plurality of fatty acid ester moieties, wherein:
   (a) from about 90% to about 100% by weight of the sucrose polyesters in the blend are selected from a group consisting of octa-, hepta-, and hexa-sucrose polyesters; and
   (b) from about 50% to about 75%, by weight, of the plural fatty acid ester moieties of the sucrose polyesters in the blend are palmitic fatty acid ester moieties, with the balance of the fatty acid ester moieties of the sucrose polyesters in the blend comprising a carbon chain independently of $C_{12}$-$C_{14}$ or $C_{18}$-$C_{22}$ carbon chains; or
   (c) from about 50% to about 90% by weight of the plural fatty acid ester moieties of the sucrose polyesters in the blend comprise a $C_{16}$ carbon chain, with the balance of the fatty acid ester moieties of the sucrose polyesters in the blend comprising a carbon chain independently of $C_{12}$-$C_{14}$ or $C_{18}$-$C_{22}$ carbon chains.

2. The composition according to claim 1, wherein about 10% to about 50% by weight of the plural fatty acid ester moieties of the sucrose polyesters in the blend comprise an unsaturated carbon chain.

3. The composition according to claim 1, wherein about 25% to about 50% by weight of the plural fatty acid ester moieties of the sucrose polyesters in the blend comprise an unsaturated carbon chain.

4. The composition according to claim 1, wherein the composition has a degree of crystallization at 25° C. of about 15% to about 40%, and a degree of crystallization at 5° C. of about 70% to about 95%.

5. The composition according to claim 1, wherein the composition has a degree of crystallization at 25° C. of about 22% to about 30%, and a degree of crystallization at 5° C. of about 80% to about 90%.

6. The composition according to claim 1, wherein the fatty acid ester moieties are derived from an edible oil that comprises at least one palmitic fatty acid.

7. The composition according to claim 1, wherein the fatty acid ester moieties are derived from an oil selected from a group consisting of coconut oil, babassu oil, cottonseed oil, cottonseed stearin, palm oil, palm olein, palm stearin, palm kernel oil and combinations thereof.

8. The composition according to claim 1 comprising:
   (a) from about 60% to about 99%, based on a total weight of the sucrose polyester blend, of sucrose polyesters having a solid content of about 1% to about 10% at about 40° C.; and
   (b) from about 1% to about 40%, based on the total weight of the sucrose polyester blend, of sucrose polyesters having a complete melting point of from about 40° C. to about 100° C.;
   wherein the composition exhibits a thixotropic area of from about 50,000 to about 300,000 pascals/second at 33.3° C.

9. The composition according to claim 1 comprising, based on a total weight of the sucrose polyester blend, from about 0% to about 0.5% penta-sucrose polyesters.

10. The composition according to claim 1, wherein the sucrose polyester blend comprises, based on a total weight of the sucrose polyester blend, a Solid Fat Index of:
    (a) from about 45% to about 85% solids at 10° C.;
    (b) from about 10% to about 50% solids at 30° C.; and
    (c) from about 1% to about 10%, solids at 40° C.

11. A process of making the composition according to claim 1, comprising a step of introducing a sucrose molecule to transesterify an ester, the ester being produced via esterifying a fractionated oil that comprises a palmitic fatty acid ester content of from about 50% to about 90% by weight with a lower alcohol.

12. A process of making the composition according to claim 1, comprising a step of introducing a sucrose molecule to transesterify a fractionated oil that comprises a palmitic fatty acid ester content of from about 50% to about 90% by weight.

13. The process according to claim 12, wherein the oil comprises an edible oil.

14. The process according to claim 12, wherein the oil comprises one selected from a group consisting of coconut oil, babassu oil, cottonseed oil, cottonseed stearin, palm oil, palm olein, palm stearin, palm kernel oil and combinations thereof.

15. A process of making the composition according to claim 1, comprising the steps of:
    (a) fractionating an oil or a methyl ester derived from an oil to produce a fractionated oil or a fractionated methyl ester comprising a palmitic fatty acid ester content of from about 50% to about 90% by weight; and
    (b) introducing a sucrose molecule to transesterify the oil or the methyl ester comprising the palmitic fatty acid ester content of from about 50% to about 90% by weight to produce an esterified sucrose polyesters comprising a palmitic fatty acid content of from about 50% to about 90% by weight.

16. The process according to claim 15, wherein the oil comprises an edible oil.

17. The process according to claim 15, wherein the oil comprises one selected from a group consisting of coconut oil, babassu oil, cottonseed oil, cottonseed stearin, palm oil, palm olein, palm stearin, palm kernel oil and combinations thereof.

18. A shortening composition comprising the composition according to claim 1.

* * * * *